US00PP10541P

United States Patent [19]

DeClercq

[11] Patent Number: Plant 10,541

[45] Date of Patent: Aug. 4, 1998

[54] SPATHIPHYLLUM PLANT NAMED 'POLLUX'

[75] Inventor: Danny DeClercq, Destelbergen, Belgium

[73] Assignee: Milestone Agriculture, Inc., Apopka, Fla.

[21] Appl. No.: 842,012

[22] Filed: Apr. 23, 1997

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—C. A. Whealy

[57] ABSTRACT

A distinct cultivar of Spathiphyllum plant named Pollux, characterized by its very compact plant habit; moderate vigor; rapid growth rate; large dark green leaves are held horizontal to the petiole; early flowering numerous white flowers that are positioned just above the foliage on strong and erect peduncles; and long-lasting flowers.

1 Drawing Sheet

The present invention relates to a new and distinct cultivar of Spathiphyllum plant, botanically known as Spathiphyllum, and hereinafter referred to by the cultivar name Pollux. The new Spathiphyllum will be marketed under the name Misty.

The new cultivar is a product of a planned and controlled breeding program conducted by the inventor in Lochristi, Belgium. The objective of the breeding program is to create new compact Spathiphyllum cultivars with short peduncles, good plant form, and early flowering. The new cultivar originated from a deliberate cross by the inventor between the proprietary Spathiphyllum selection SP 13 as the female or seed parent and the proprietary Spathiphyllum selection SP 5 as the male or pollen parent. The cultivar Pollux was discovered and selected by the inventor as a plant within the progeny of the stated cross in a controlled environment in Lochristi, Belgium. Compared to the female parent, the new Spathiphyllum has smaller flowers and compared to the male parent, the new Spathiphyllum has larger leaves.

Asexual propagation of the new cultivar, by tissue culture, at Lochristi, Belgium, has shown that the unique features of this new Spathiphyllum plant are stable and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Apopka, Fla., under commercial greenhouse conditions.

The following traits have been repeatedly observed and are determined to be the unique characteristics of Pollux. These characteristics in combination distinguish Pollux as a new and distinct cultivar:

1. Very compact plant habit.
2. Moderate vigor, rapid growth rate.
3. Dark green leaves that are held horizontal to the petiole.
4. Early flowering.
5. Numerous white flowers that are positioned just above the foliage on strong and erect peduncles.
6. Long-lasting flowers.

The new Spathiphyllum can be compared to the nonpatented commercial cultivar Petite. However in side-by-side comparisons conducted in Lochristi, Belgium, plants of the new Spathiphyllum have shorter peduncles and larger leaves than plants of the cultivar Petite.

The accompanying colored photograph illustrates the overall appearance of the new cultivar, showing the colors as true as it is reasonably possible to obtain in colored reproductions of this type. The photograph comprises a side perspective view of a typical potted plant of Pollux.

In the following description, color references are made to The Royal Horticultural Society Colour Chart except where general terms of ordinary dictionary significance are used.

Botanical classification: Spathiphyllum cultivar Pollux.

Parentage:

*Female parent.*—Proprietary Spathiphyllum selection SP 13.

*Male parent.*—Proprietary Spathiphyllum selection SP 5.

Propagation: By division or by tissue culture.

*Time to initiate roots.*—Winter: About 10 days at 20° C. Summer: About 5 days at 26° C.

*Rooting habit.*—Freely branching, numerous fleshy roots.

Plant description:

*Plant shape.*—Upright, inverted triangle, symmetrical.

*Growth habit.*—Erect when young, becoming outwardly arching as leaves develop. Numerous side shoots give plants a full, dense appearance. Compact, appropriate for 10 to 12.5-cm containers.

*Plant height.*—About 18 cm from soil level to top of leaf plane.

*Plant vigor.*—Moderate vigor, rapid growth rate.

*Crop time.*—During the summer, 26° C. production temperatures, about 63 days are required to produce a 10-cm plant. During the winter, 20° C. production temperatures, about 84 days are required to produce a 10-cm plant.

*Foliage description.*—Leaf shape: Lanceolate. Leaf length: About 18 cm. Leaf width: About 7 cm. Margin: Entire, slight waviness. Leaf surface: Flat, rugose. Leaf tip: Acuminate. Leaf base: Cuneate. Leaf aspect: Mature leaves held perendicular to petiole, with further development, leaves begin to droop. Leaf texture: Leathery, smooth, glabrous, durable. Abaxial surface, glossy; adaxial surface, dull. Leaf color: Young, top side: 147A, glossy. Young, under side: Darker than 147B. Mature, top side: 147A, glossy. Mature, under side: Darker than 147B. Venation: Top side: 147A, sunken. Under side: Darker than 147B, prominent. Petiole length, primary shoots: About 15 cm. Petiole diameter, primary shoots, just below geniculum: About 3 mm. Geniculum diameter, primary shoots: About 3.5 mm. Petiole wing, primary shoots: Apparent on lower 70 to 80% of mature leaf petiole. Petiole color: Young: 137A. Fully developed: Winged area: 137A/137B. Above winged area: 137B. Geniculum: 137A.

Flower description:

*Flower arrangement.*—Concave spathe with spadix held 5 to 10 cm above the foliage. Numerous flowers arise from leaf axils.

*Flower longevity.*—Flowers are long-lasting, generally maintaining white color for about 12 weeks on the plant depending on light and temperature levels.

*Spathe.*—Shape: Ovate, lanceolate. Size: Length: About 10 cm. Width: About 4.5 cm. Aspect: Concave, curving over the spadix. Color: Before unrolling: White, 155D. Open flower: White, 155D, with green, 144A, midvein; eventually turning green, 144A, with age.

*Spadix.*—Size: Length: About 3.8 cm. Diameter: About 1 cm. Color: White, 155D, becoming green, 144A, with age. Pollen: White, abundant.

*Peduncle.*—Aspect: Strong and erect. Size: Length: About 23 cm. Diameter: About 3 mm. Color: 137A.

Disease resistance: No known Spathiphyllum diseases observed to date on plants grown under commercial greenhouse conditions.

Seed development: Seed development has not been observed.

It is claimed:

1. A new and distinct cultivar of Spathiphyllum plant named Pollux, as illustrated and described.

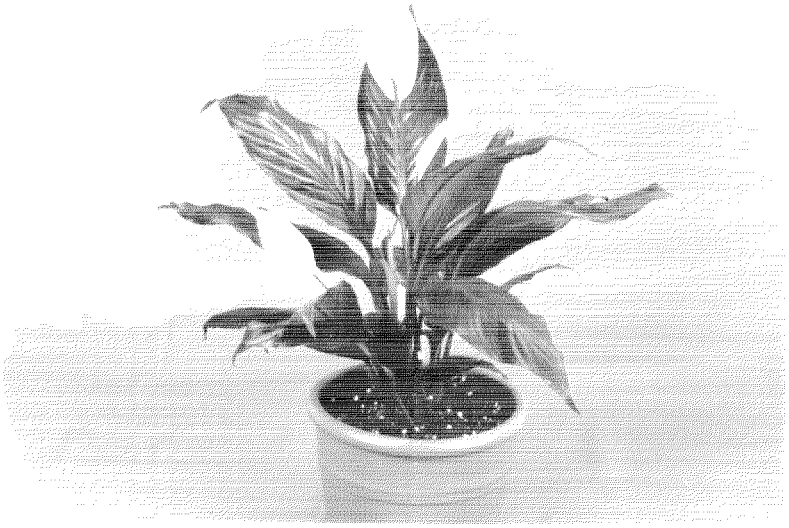

* * * * *